US006624317B1

(12) United States Patent
Lee et al.

(10) Patent No.: US 6,624,317 B1
(45) Date of Patent: Sep. 23, 2003

(54) TAXOID CONJUGATES AS ANTIMITOTIC AND ANTITUMOR AGENTS

(75) Inventors: Kuo-Hsiung Lee, Chapel Hill, NC (US); Qian Shi, Chapel Hill, NC (US); Kenneth F. Bastow, Chapel Hill, NC (US); Hui-Kang Wang, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 89 days.

(21) Appl. No.: 09/669,156

(22) Filed: Sep. 25, 2000

(51) Int. Cl.[7] ............... C07D 305/00; C07D 407/00; C07D 493/00; A01N 43/42
(52) U.S. Cl. ............. 549/510; 549/511; 514/280; 514/283; 514/285; 514/297; 514/298; 514/449; 536/4.1; 536/17.1; 536/17.2; 536/18.1; 536/18.2; 536/18.5
(58) Field of Search ................ 549/510, 511; 514/449, 280, 283, 285, 297, 463, 298; 536/4.1, 17.1, 17.2, 18.1, 18.2, 18.5

(56) References Cited

U.S. PATENT DOCUMENTS

| | | | |
|---|---|---|---|
| 4,045,565 A | | 8/1977 | Le Pecq et al. |
| 4,698,423 A | | 10/1987 | Honda et al. |
| 5,066,645 A | | 11/1991 | Ohnuma et al. |
| 5,122,368 A | | 6/1992 | Greenfield et al. |
| 5,354,864 A | | 10/1994 | Watanabe et al. |
| 5,378,456 A | | 1/1995 | Tsou |
| 5,407,940 A | | 4/1995 | Bisagni et al. |
| 5,411,984 A | | 5/1995 | Kingston et al. |
| 5,498,611 A | | 3/1996 | Bisagni et al. |
| 5,498,738 A | * | 3/1996 | Karvinen et al. |
| 5,508,447 A | | 4/1996 | Magnus |
| 5,560,923 A | | 10/1996 | Rahman et al. |
| 5,571,914 A | | 11/1996 | Terada et al. |
| 5,614,645 A | | 3/1997 | Kingston et al. |
| RE35,524 E | | 6/1997 | Saulnier et al. |
| 5,650,399 A | | 7/1997 | Rokita et al. |
| 5,744,454 A | | 4/1998 | Suarato et al. |
| 5,843,910 A | | 12/1998 | Bombardelli et al. |
| 5,858,397 A | | 1/1999 | Lim et al. |
| 5,880,160 A | | 3/1999 | Bombardelli et al. |
| 5,892,063 A | * | 4/1999 | Zheng et al. |
| 5,939,428 A | | 8/1999 | Su et al. |
| 5,958,889 A | | 9/1999 | Takeuchi et al. |
| 5,973,204 A | | 10/1999 | Bombardelli |
| 6,028,206 A | | 2/2000 | Chattopadhyay et al. |
| 6,136,988 A | * | 10/2000 | Murray et al. |

| 6,207,673 B1 | 3/2001 | Lee et al. |
|---|---|---|

FOREIGN PATENT DOCUMENTS

| WO | WO95/20567 | 8/1995 |
|---|---|---|
| WO | WO96/01127 | 1/1996 |
| WO | WO97/44026 | 11/1997 |
| WO | WO98/40104 | 9/1998 |

OTHER PUBLICATIONS

International Search Report for International Application Ser. No. PCT/US01/29917 dated Jan. 2, 2003.
Bostock–Smith, Clare E., et al., *Molecular Recognition between a New Pentacyclic Acridinium Salt and DNA Sequences Investigated by Optical Spectroscopic Techniques, Proton Nuclear Magnetic Resonance Spectroscopy, and Molecular Modeling*, Biochemistry, vol. 38, pp. 6723–6731 (1999).

* cited by examiner

*Primary Examiner*—James O. Wilson
*Assistant Examiner*—Traviss C. McIntosh, III
(74) *Attorney, Agent, or Firm*—Myers Bigel Sibley & Sajovec (57) ABSTRACT

Compounds according to formula I:

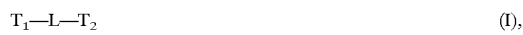

wherein $T_1$ is a taxoid group, preferably of Formula II:

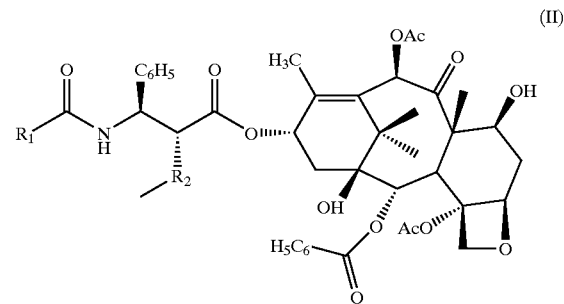

wherein $R_1$ is $C_6H_5$; $R_2$ is O; L is a linking group; and $T_2$ is a substituent selected from the group consisting of epipodophyllotoxin, amsacrine, ellipticine, anthracycline antibiotic, mitoxantrone, and colchicine groups, and pharmaceutically acceptable salts thereof, are provided herein. The compounds are useful in, among other things, treating tumors or cancer in subjects in need thereof, inducing cellular differentiation, and inhibiting cellular mitosis.

19 Claims, 3 Drawing Sheets

TAXOID CONJUGATES AS ANTIMITOTIC AND ANTITUMOR AGENTS

This investigation was made with government support under Grant Number CA-17625 from the National Cancer Institute. The government has certain rights to this invention.

FIELD OF THE INVENTION

The present invention concerns taxoid conjugates, pharmaceutical formulations containing the same, and methods of use thereof as antimitotic and antitumor agents, particularly for the treatment of tumors such as breast cancer and ovarian cancer.

BACKGROUND OF THE INVENTION

The complex diterpenoid paclitaxel (1) is an exciting new anticancer drug, which is currently in clinical use against ovarian and breast cancer under the trademark TAXOL®. See generally Merck Index, Monograph No. 7117 (12$^{th}$ Ed. 1996).

Paclitaxel acts by an unusual mechanism: promoting microtubule assembly. Since the discovery of paclitaxel as an antimitotic antitumor agent, its chemistry and structure activity relationship have been extensively studied in order to develop more potent derivatives and to overcome its low water solubility and drug resistance problems. Much research has focused on the modifications at C2, C4, C7, C9, C10, and the C13 side chain, and the resulting structure-activity relationships have led to more potent paclitaxel derivatives. Also, selective modification of the 2'-hydroxyl led to synthesis of a series of water-soluble derivatives (A. Mathew et al., J Med. Chem. 1992, 35, 145–151). However, drug resistance is still a major problem associated with paclitaxel, and novel derivatives are highly desirable.

Previously, we synthesized and evaluated two compounds (3 and 4) that are conjugates of a camptothecin (CPT) derivative and an etoposide (5) analog (K. Bastow et al., Bioorg. Med Chem. 1997, 5, 1481–1488). Both compounds induced protein-linked DNA breaks (PLDB) in a concentration dependent manner in drug treated cells. The drug induced PLDB could be mediated by both DNA topoisomerases (topo) I and II. The two conjugates were more active than CPT against CPT-resistant cells and than etoposide against etoposide-resistant cells. Over-expression of the multiple drug resistant proteins GP 170 or MRP had little impact on the cytotoxicity. The compounds were equally cytotoxic as CPT in CPT-sensitive or etoposide-resistant cells and as etoposide in CPT-resistant cells. In vivo, one conjugate (3) was more active than either etoposide or CPT against human KB and DU-145 tumor cells in nude mice. This topo I and II dual inhibitory property as well as the unique antitumor action of these CPT-etoposide analog conjugates suggests that such bimolecular models should be further explored as anticancer drugs.

SUMMARY OF THE INVENTION

A first aspect of the present invention is a compound according to formula I:

$$T_1-L-T_2 \quad (1)$$

wherein:
$T_1$ is a taxoid group, preferably of Formula II:

wherein $R_1$ is $C_6H_5$, and $R_2$ is O;
L is a linking group; and
$T_2$ is a substituent selected from the group consisting of epipodophyllotoxin, amsacrine, ellipticine, anthracycline antibiotic, mitoxantrone, mitomycin, quinolone, and colchicine groups;
or a pharmaceutically acceptable salt thereof.

A second aspect of the present invention is a pharmaceutical formulation comprising a compound according to Formula I above in a pharmaceutically acceptable carrier.

A further aspect of the present invention is a method of treating a tumor, particularly a solid tumor, comprising administering to a subject in need thereof a treatment effective amount of a compound according to Formula I above. Examples of tumors that may be treated include, but are not limited to, lung cancer, colon cancer, central nervous system cancers, melanoma, ovarian cancer, prostate cancer and breast cancer tumors.

A further aspect of the present invention is a method of treating cancer in a subject in need thereof, the method comprising administering to the subject an effective cancer treating amount of a compound according to Formula I. Illustrative cancers that may be treated by the present invention include, but are not limited to, small cell lung cancer, testicular cancer, lymphoma, leukemia, esophageal cancer, stomach cancer, colon cancer, breast cancer, central nervous system cancer, liver cancer and prostate cancer.

A further aspect of the present invention is a method of inducing cellular differentiation, the method comprising contacting (in vivo or in vitro) a cancer cell with a differentiation effective amount of a compound according to Formula I above.

A further aspect of the present invention is method of inhibiting cellular mitosis, comprising contacting (in vivo or in vitro) a cell with a mitosis inhibiting amount of a compound according to Formula I above.

The foregoing and other objects and aspects of the present invention are explained in greater detail in the drawings herein and the specification set forth below.

DETAILED DESCRIPTION OF THE PREFERRED EMBODIMENTS

"Alkyl" as used herein refers to linear or branched, saturated or unsaturated hydrocarbon chains, typically C1–C4, including for example, methyl, ethyl, propyl, isopropyl, butyl, isobutyl, and tert-butyl groups.

"Alkoxy" as used herein refers to linear or branched, saturated or unsaturated oxo-hydrocarbon chains, including for example methoxy, ethoxy, propoxy, isopropoxy, butoxy, and t-butoxy.

"Amino" as used herein refers to the substituent —NR$_1$R$_2$, where R$_1$ and R$_2$ are each independently selected from the group consisting of H and C1–C4 alkyl.

"Halo," "halide," or "halogen" as used herein refer to fluorine, chlorine, bromine, and iodine.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

1. Active compounds

Active compounds of the present invention can be synthesized in accordance with known procedures, or variations thereof that will be apparent to skilled persons in light of the disclosure set forth herein. In general, active compounds of the present invention have the formula:

$$T_1—L—T_2 \quad (I)$$

wherein T$_1$ is a taxoid group, L is a linking group, and T$_2$ is a substituent selected from the group consisting of epipodophyllotoxin, anisacrine, ellipticine, anthracycline antibiotic, mitoxantrone, mitomycin, quinoline, and colchicine groups. Active compounds as used herein include the pharmaceutically acceptable salts thereof. The various groups that can be used in conjunction with formula I above are discussed in greater detail below.

Taxoid groups. A taxoid group that can be used to carry out the present invention is represented by Formula II:

wherein R$_1$ is C$_6$H$_5$, and R$_2$ is O. "Ac" as used herein refers to a substituent of the formula —C(O)CH$_3$.

Paclitaxel is known and can be produced in accordance with known techniques. See generally Merck Index, Monograph No. 7117 (12$^{th}$ Ed. 1996).

Examples of taxoid groups that can be used to carry out the present invention include, but are not limited to, those described in U.S. Pat. No. 5,614,645 to Kingston et al.; U.S. Pat. No. 6,028,206 to Chattopadhyay et al; 5,411,984 to Kingston et al.; and U.S. Pat. No. 5,508,447 to Magnus. Covalent linkages of the compounds disclosed in these references to linking group L may be formed at the same location and in the same manner as given in connection with compounds of Formula II above.

Epipodophyllotoxin groups. Examples of epipodophyllotoxin groups that may be used to carry out the present invention include compounds of formula III-A:

wherein:

R$_{10}$, R$_{11}$, R$_{12}$, R$_{13}$, R$_{,15}$ and R$_{16}$ are each independently selected from the group consisting of H, alkyl, hydroxy, alkoxy, alkylhydroxy, and halo;

R$_{14}$ is selected from the group consisting of H, alkyl, hydroxyl, alkoxy, alkylhydroxy, halo, and phosphate salt; and R$_{17}$ is NH or is absent.

Examples of epipodophyllotoxin groups that may be used in carrying out the present invention include, but are not limited to, those described in U.S. Pat. No. Re. 35,524 to Saulnier et al.; U.S. Pat. No. 5,571,914 to Terada et al.; and U.S. Pat. No. 5,066,645 to Ohnuma et al. Covalent linkages of the compounds disclosed in these references to linking group L may be formed at the same location and in the same manner as given in connection with compounds of Formula III-A above.

Amsacrine groups. Examples of amsacrine groups that may be used to carry out the present invention include those of formula III-B wherein R$_{20}$ and R$_{21}$ are each independently selected from the group consisting of H, alkyl, hydroxy, alkoxy and alkylhydroxyl;

R$_{22}$ and R$_{23}$ are each independently selected from the group consisting of H, alkyl, hydroxy, alkoxy, alkylhydroxy, and halo; and R$_{24}$ is NH or is absent.

Examples of amsacrine groups that may be used to carry out the present invention include, but are not limited to, those described in U.S. Pat. No. 5,358,864 to Watanabe et al.; and U.S. Pat. No. 5,939,428 to Su et al. (See, e.g., C. Bostock-Smith, *Biochemistry* 38, 6723–6731 (1999) for m-AMSA). Covalent linkages of the compounds disclosed in these references to linking group L may be formed at the same location and in the same manner as given in connection with compounds of Formula III-B above.

Ellipticine groups. Examples of ellipticine groups that may be used to carry out the present invention include, but are not limited to, compounds of formula III-C:

(III-C)

wherein:

$R_{30}$ is H or alkyl, or is absent;

$R_{31}$ is H, alkyl, hydroxy, alkoxy, alkyhyroxy, halo, or —C(O)—N($R_{36}$)—(CH$_2$)$_n$—N($R_{37}$)($R_{38}$) wherein $R_{36}$, $R_{37}$, and $R_{38}$ are each independently selected from the group consisting of H and alkyl and n is an integer from 1 to 6;

$R_{32}$ and $R_{33}$ are each independently selected from the group consisting of H, alkyl, hydroxy, alkoxy, alkylhydroxy, and halo;

$R_{34}$ is H or alkyl; and $R_{35}$ is O or is absent.

Examples of ellipticine groups that may be used to carry out the present invention include, but are not limited to, those disclosed in U.S. Pat. No. 5,407,940 to Bisagni et al.; U.S. Pat. No. 5,498,611 to Bisagni et al.; 4,698,423 to Honda et al.; and U.S. Pat. No. 4,045,565 to LePecq et al., Covalent linkages of the compounds disclosed in these references to linking group L may be formed at the same location and in the same manner as given in connection with compounds of Formula III-C above.

Anthracycline antibiotic groups. Examples of anthracycline antibiotic groups that can be used to carry out the present invention include, but are not limited to, compounds of formula III-D:

(III-D)

wherein:

$R_{40}$ is H, alkyl, hydroxy, alkoxy, alkylhydroxy, or halo;

$R_{41}$ is hydroxyl O— or a covalent bond;

$R_{42}$ is alkyl, alkylhydroxyl, CH$_2$O— or CH$_2$—; and $R_{43}$ and $R_{44}$ are each independently selected from the group consisting of H and hydroxy;

$R_{45}$ is hydroxy or NH$_2$; and $R_{46}$ is H or halo;

subject to the provisos that if $R_{41}$, is not O— or a covalent bond, then $R_{42}$ is CH$_2$O— or CH$_2$—; and if $R_{42}$ is not CH$_2$O— or CH$_2$— then $R_{41}$ is O— or a covalent bond.

Examples of anthracycline antibiotic groups that may be used to carry out the present invention include, but are not limited to, those disclosed in U.S. Pat. No. 5,958,889 to Takeuchi et al.; U.S. Pat. No. 5,560,923 to Rahman et al.; and U.S. Pat. No. 5,744,454 to Suarato et al. Covalent linkages of the compounds disclosed in these references to linking group L may be formed at the same location and in the same manner as given in connection with compounds of Formula III-D above.

Mitoxantrone groups. Examples of mitoxantrone groups that may be used to carry out the present invention include compounds of formula III-E:

(III-E)

wherein $R_{50}$, $R_{51}$, $R_{52}$ and $R_{53}$ are each independently selected from the group consisting of OH or O—; subject to the proviso that one of $R_{50}$, $R_{51}$, $R_{52}$ and $R_{53}$ is O—.

Mitoxantrone compounds that may be used to carry out the present invention are described in U.S. Pat. No. 5,378,456 to Tsou and U.S. Pat. No. 5,858,397 to Lim et al. Covalent linkages of the compounds disclosed in these references to linking group L may be formed at the same location and in the same manner as given in connection with compounds of Formula III-E above.

Mitomycin groups. Examples of mitomycin groups that may be used to carry out the present invention include compounds of formula III-F:

(III-F)

wherein:

X is NH$_2$, NH—, or an aliphatic amine;

$R_{71}$ is alkyl or halo $R_{72}$ is hydroxy or alkoxy;

$R_{73}$ is H or absent; and

Y is H or alkyl.

Colchicine groups. Examples of colchicine groups that may be used to carry out the present invention include compounds of formula III-G:

(III-G)

wherein:
R$_{60}$ and R$_{61}$, are each independently H, alkyl, hydroxy, O—, or alkoxy;
R62 is H, NH$_2$, NH—, OH, O—, =O, or NHCOCH$_3$, and X is S or O,
subject to the proviso that one of R$_{60}$ or R$_{61}$, is O—, or R$_{62}$ is either NH— or O—, (to provide a linking group to the conjugate).

Examples of colchicine groups that may be used to carry out the present invention include, but are not limited to, those described in U.S. Pat. No. 5,880,160 to Bombardelli et al., 5,973,204 to Bombardelli, and U.S. Pat. No. 5,843,910 to Bombardelli et al. Covalent linkages of the compounds disclosed in these references to linking group L may be formed at the same location and in the same manner as given in connection with compounds of Formula III-G above.

Quinolone groups. Examples of quinolone groups that may be used to carry out the present invention include, but are not limited to, compounds of Formula III-H:

(III-H)

wherein:
R$_{81}$ is selected from the group consisting of H, hydroxy, lower alkyl, lower alkoxy, hydroxy, halo, and amino (preferably H or lower alkyl; most preferably H);
R$_{82}$ is is selected from the group consisting of H, hydroxy, lower alkyl, lower alkoxy, hydroxy, halo, and amino (preferably H or lower alkyl; most preferably H);
R$_{83}$ is is selected from the group consisting of H, hydroxy, lower alkyl, lower alkoxy, hydroxy, halo, and amino (preferably H or lower alkyl; most preferably H);
R$_{84}$ is is selected from the group consisting of H, hydroxy, lower alkyl, lower alkoxy, hydroxy, halo, and amino (preferably H or lower alkyl; most preferably H);
R$_{85}$ is each independently selected from the group consisting of H, hydroxy, lower alkyl, lower alkoxy, hydroxy, halo, and amino (preferably H or lower alkyl; most preferably H); and
n is 0, 1, 2, 3, or 4 (it being understood that, when n is 0, then all positions are substituted by H) (in one preferred embodiment, at least one of R$_{85}$ is present and is F).

Linking groups. Linking groups (linkers, linking arms, etc.) that may be used to form covalent conjugates of two functional moieties are known in the art. The particular linking group employed in carrying out the present invention is not critical, and linking groups that may be used include, but are not limited to, those disclosed in U.S. Pat. No. 5,650,399 to Rokita et al., and U.S. Pat. No. 5,122,368 to Greenfield et al. In general, the linking group may comprise an aliphatic, aromatic, or mixed aliphatic and aromatic group (e.g., alkyl, aryl, alkylaryl, etc.) and contain one or more hetero atoms such as N, O, S, etc. For example, the linking group L may be a compound of the formula —L$_a$—L$_b$—, where L$_b$ is present or absent and L$_a$ and L$_b$ are each independently selected from the group consisting of:

and wherein:
a is 0–3 and b is 0–3; and
R$_{70}$ is selected from the group consisting of alkylene, alkenyl, and arylenyl.

Figure 2:
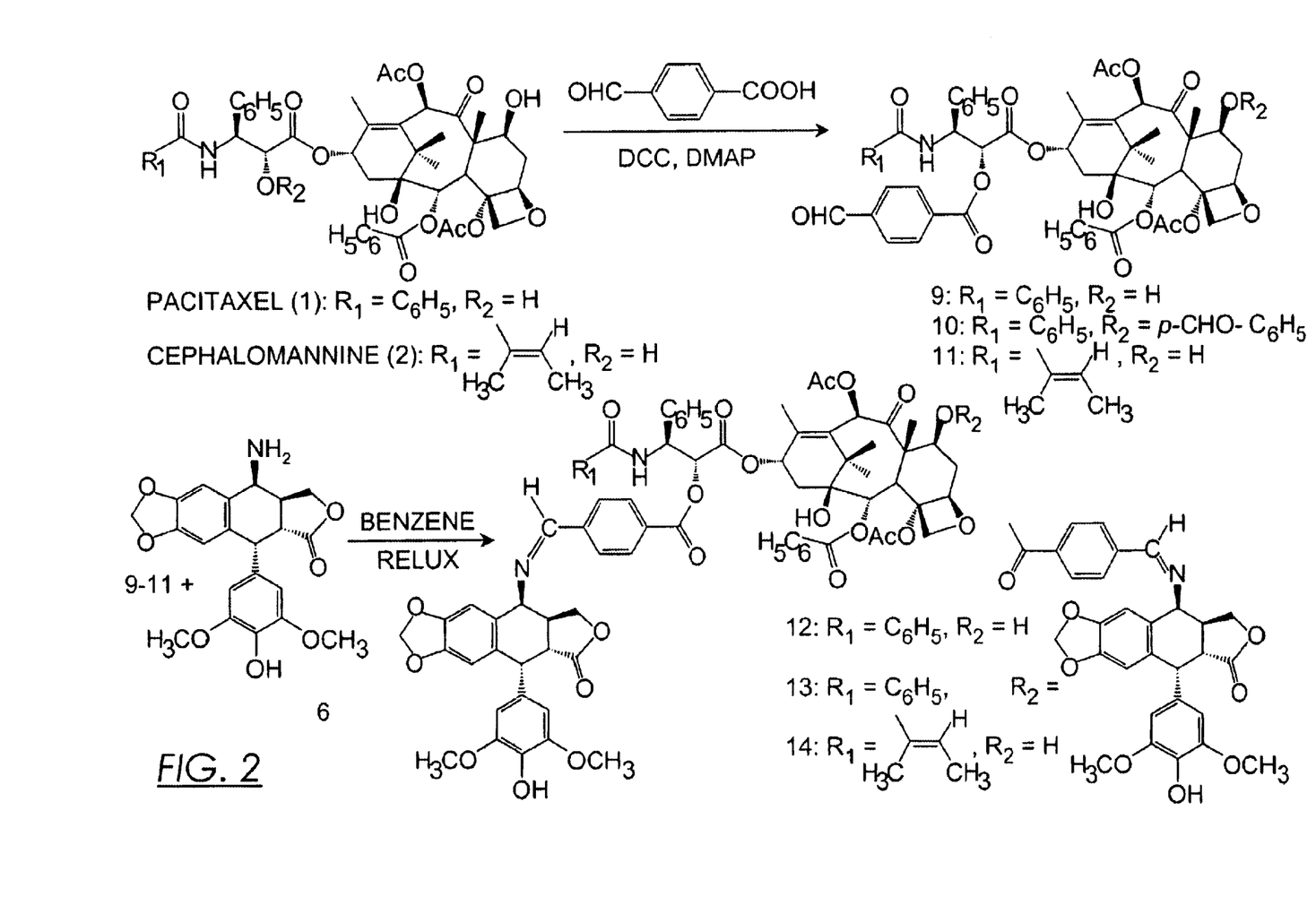
FIG. 2 illustrates a synthesis, Scheme 1, for making compounds of the present invention.

Synthesis of compounds of the present invention may be determined by the particular linking chemistry employed. For example, the synthesis of a series of 2'-(4"-O-demethyl epipodophyllotoxin) taxoids is given in Scheme 1. Numerous variations of the synthetic chemistry will be readily apparent to those skilled in the art.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, suiftiric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations

The active compounds described above may be formulated for administration in a pharmaceutical carrier in accordance with known techniques. See, e.g., Remington, The Science And Practice of Pharmacy ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01% or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations maybe prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unitdose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bistris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration

The active compounds described herein inhibit tubulin polymerization and/or have antimitotic activity. Such compounds are useful for the treatment of conditions including psoriasis, gout, papiloma, warts, and various tumors, particularly solid tumors, including but not limited to lung cancer (e.g., non-small cell lung cancer), colon cancer, central nervous system cancers, melanoma, ovarian cancer, prostate cancer and breast cancer.

Subjects to be treated by the methods of the present invention are typically human subjects although the methods of the present invention may be useful with any suitable subjects known to those skilled in the art, and particularly mammalian subjects including, in addition to humans, horses, cows, dogs, rabbits, fowl, sheep, and the like. As noted above, the present invention provides pharmaceutical formulations comprising the compounds of Formula I, or pharmaceutically acceptable salts thereof, in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting Examples.

EXAMPLES

A. Materials and Methods.

Paclitaxel and cephalomannine were kind gifts of Yung-Shin Pharm. Co., Taiwan the proton nuclear magnetic resonance ($^1$H NMR) spectra were measured on a Bruker AC-300 spectrometer or Varian Inova 600 with $Me_4Si$ (TMS) as the internal reference and $CDCl_3$ as solvent. Atmosphere Pressure chemical Ionization (APCI) Mass was determined by PE Sciex API 150 Mass spectrometer. Thin-layer chromatography (TLC) silica gel plates were purchased from Alltech, Inc.

General Procedure for Synthesizing (4-Formyl)benzoyl taxoids. To a solution of taxoid in anhydrous methylene chloride was added an equal molar ratio of 4-carboxylbenzaldehyde (except 2 equivalents were used for 10) and 4-dimethylaminopyridine (4-DMAP). To the mixture then was added an equal molar amount of 1,3-dicyclohexylcarbodiimide (DCC). The mixture was stirred under $N_2$ at room temperature for 24 h with TLC monitoring. The dicyclohexylurea precipitate was filtered and washed with $CH_2Cl2$. The filtrate was concentrated to afford a white solid, which was further chromatographed over silica gel with an Elutflash® flashed silica gel column and eluted with $CH_2Cl_2$:MeOH-10:0 to 20:1 to yield the desired 9, as a white powder.

2'-(4-Formyl)benzoyl paclitaxel (9). Yield 92% (starting with 11.7 g of paclitaxel); amorphous; $^1$H NMR theta ($CDCl_3$) see Table 1; APCI-MS m/z 986.6 (M+H$^+$).

2',7-Bis(4-Formyl)-benzoyl paclitaxel(10). Same as general procedure except 1 mmol of paclitaxel and 2 mmol of 4-carboxylbenzaldehyde and DCC were used. Yield 95% (starting with 19.7 mg of paclitaxel). $^1$H NMR theta ($CDCl_3$) see Table 1; APCI-MS m/z 1118.8 (M+H$^+$).

2'-(4-Formyl)benzoyl cephalomannine (11). Yield 95% (starting with 205 mg of cephalomannine); amorphous $^1$H NMR theta ($CDCl_3$) see Table 1; APCI-MS m/z 964.6 (M+H$^+$).

General Procedure for Synthesizing Target Compounds 12–16. To a solution of mono or bis 2'-(4-formyl)benzoyl taxoid (9–11) in anhydrous benzene was added an appropriate epipodophyllotoxin derivative (1 or 2 equiv. 6 or 8). The mixture was heated to reflux with a Dean Stark trap for 24 hrs. The solvent was distilled and the residue was purified by silica gel column chromatography eluting with $CH_2Cl_2$:MeOH=20:1 to afford the desired compounds.

Conjugate 12. A yellow powder in 92% yield [starting with 22.5 mg (0.023 mmol) of 9 and 10.0 mg. (0.025 mmol) of 4'-O-demethyl-4beta-amino-4-desoxypodophyllotoxin (6)]; amorphous; ¹H NMR theta (CDCL₃) see Table 1; APCI-MS m/z 1367.7 (M+H⁺).

Conjugate 13. A yellow powder in 89% yield [starting with 7.0 mg (0.006 mmol) of 2',7-bis(4-formyl)benzoyl paclitaxel (10) and 5.1 mg (0.013 mmol) of 6]; amorphous; ¹H NMR theta (CDCl₃) see Table 1; APCI-MS m/z 1864.7 (M+H⁺).

Conjugate 14. A yellowish powder in 89% yield [starting with 39 mg (0.040 mmol) of 2'-(4-formyl)benzoyl Cephalomannine (11) and 16 mg (0.040 mmol) of 6]; amorphous; ¹H NMR theta (CDCl₃) see Table 1; APCI-MS m/z 1345.8 (M +H⁺).

Conjugate 15. A yellow solid in 70% yield [starting with 20.0 mg ((0.023 mmol) of compound 9 and 10.6 mg (0.025 mmol) of 8]; amorphous ¹H NMR theta (CDCl₃) see Table 1; APCI-MSA m/z 1458.8 (M+H⁺).

Conjugate 16. A yellow solid in 85% yield [starting with 39 mg (0.040 mmol) of compound 11 and 20 mg (0.040 mmol) of 8]; amorphous, ¹H NMR theta (CDCl₃) see Table 1; APCI-MS m/z 1437.9 (M+H⁺).

Biological Assay. The in vitro cytotoxicity assay was carried out according to procedures described in Rubinstein et al. (P. Ferguson et al., *Cancer Res.* 1988, 48, 5956–5964). Drug stock solutions were prepared in DMSO, and the final solvent concentration was □2% DMSO (v/v) a concentration without effect on cell replication. The human tumor cell line panel consisted of epiderimoid carcinoma of the nasopharynx (KB), lung carcinoma (A-549), ileocecal carcinoma (HCT-8), renal cancer (CAKI-1), breast cancer (MCF-7), melanoma cancer (SKMEL-2), and ovarian cancer (1A9). The drug resistant cell line panel consisted of three KB-derivatives, -7d, -CPT, and -VCR. The properties of these cells are described elsewhere (P. Ferguson et al., *Cancer Res.* 1988, 48, 5956–5964; D. Beidler et al., *Cancer Res.* 1996, 56, 345–353). The PAX-10 and PAX-22 sub-line derivatives from 1A9 cells are resistant to paclitaxel and have mutations in beta-tubulin. They were a generous gift of Dr. P. Giannakakou (P. Giannakakou et al., *J. Biol. Chem.* 1997, 27, 17118–17125). Cells were cultured at 37° C. in RPMI-1640 with 100 ug/mL kanamycin and 10% (v/v) fetal bovine serum in a humidified atmosphere containing 5% $CO_2$. Initial seeding densities varied among the cell lines to ensure a final absorbance of 1–2.5 $A_{562}$ units. Drug exposure was for 3 days, and the $ED_{50}$ value, the drug concentration that reduced the absorbance by 50%, was interpolated from dose-response data. Each test was performed in triplicate, and absorbance reading varied no more than 5%.

Protein-Linked DNA Break and Topoisomerase 11 Activity Assays. The procedures were done according to detailed published methods (K. Bastow et al., *Bioorg. Med. Chem.* 1997, 5, 1481–1488).

B. Results and Discussion

The 2'-hydroxyl of paclitaxel is more reactive than the sterically hindered 7-hydroxyl (J. Deutsch et al., *J. Med. Chem.* 1989, 32, 788–792; N. Magri et al., *J. Org. Chem.* 1986, 51, 797–802). Therefore, a 4'-O-demethyl epipodophyllotoxin analog can be introduced selectively at the 2'-position of paclitaxel via a benzaldehyde bridge. The three mono- and bis-(4-formyl)benzoyl taxoids (9–11) were synthesized by reacting paclitaxel (1) or cephalomannine (2) with 4-carboxybenzaldehyde in the presence of 1,3-dicyclohexylcarbodiimide (DCC) and 4-dimethylaminopyridine (4-DMAP)(Scheme 1) respectively. 4'-O-Demethyl-4beta-amino-4-desoxypodophyllotoxin, 6, was synthesized according to a literature method (X. Zhou et al., *J. Med. Chem.* 1991, 34, 3346–3350). 4-O-Demethyl-4beta-(p-aminoanilino)-4-desoxypodophyllotoxin, 8, was synthesized by treating podophyllotoxin with trimethylsilyl iodide (TMSI) in methylene chloride, followed by substitution with p-nitroaniline in the presence of barium carbonate (L. Daley et al., *Terahedron Lett.* 1997, 38, 2673–2676), and finally, by hydrogenation of the resulting nitro compound. Syntheses of the desired conjugates (12–16) were accomplished by reaction of 9–11 with 6 or 8 in refluxing benzene to form an imine linkage (Scheme 1). The structures of these conjugates were confirmed unambiguously from NMR and mass spectral data. The detailed assignments of the NMR signals are listed in Table 1.

Figure 1:
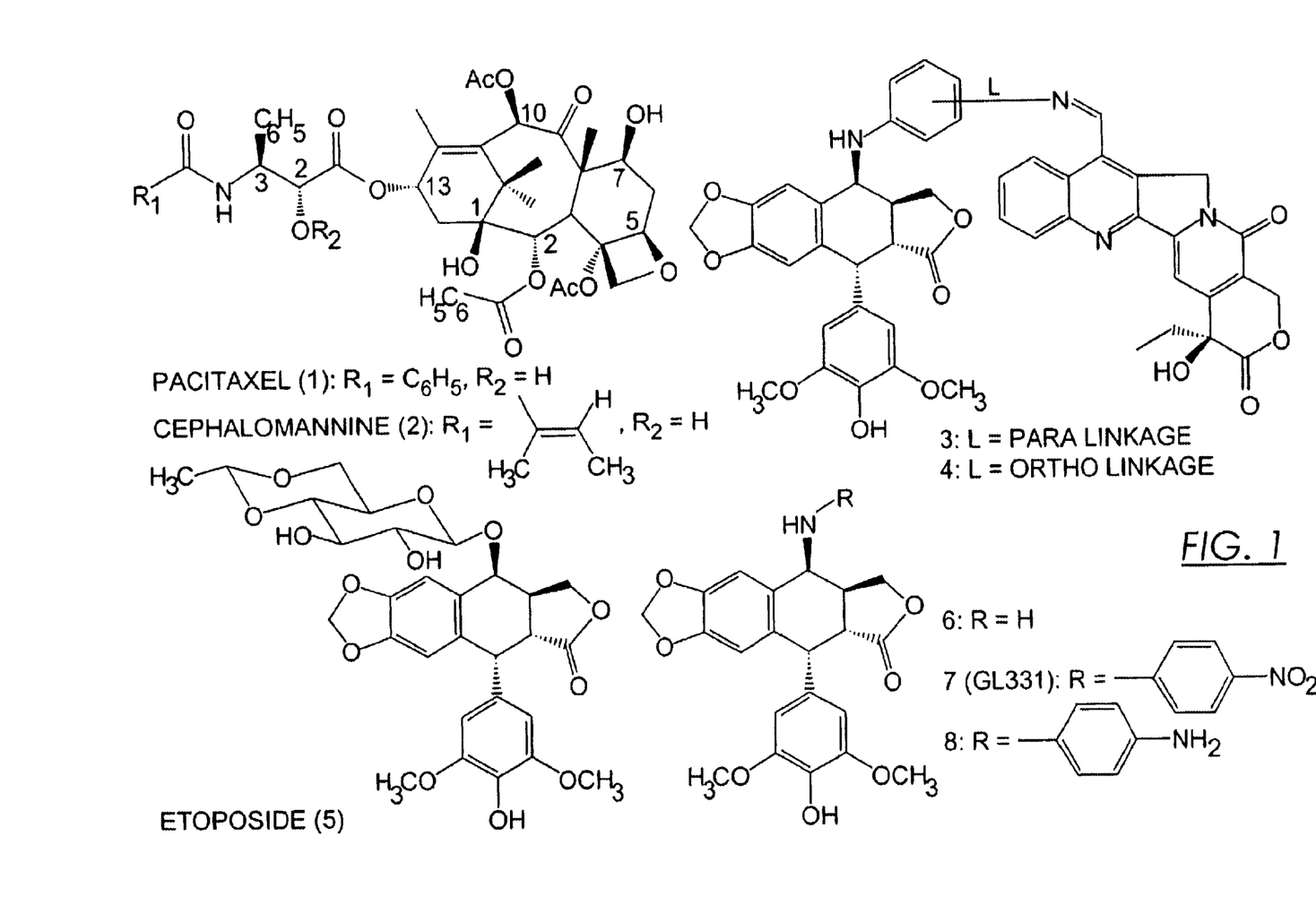
FIG. 1 illustrates the structures of various precursor compounds used to carry out the present invention.

The newly synthesized taxoid-4'-O-demethyl epipodophyllotoxin conjugates were evaluated in house using standard cytotoxicity assays in human tumor (HTCL) and drug-resistant (DRCL) cell lines. Reference compounds were paclitaxel (1), cephalomannine (2), and epipodophyllotoxins [etoposide (5) and GL-331 (7), see FIG. 1]. The HTCL panel was comprised of KB, A549, HCT-8, CAKI-1, MCF-7, SK-MEL-2, and 1A9 cell lines. Two paclitaxel-resistant 1A9 sub-lines designated as PAX-10 and PAX-22 were also tested as part of the DRCL panel. Other resistant-cell lines were KB derivatives expressing various mechanisms or multi-drug resistance as described elsewhere (P. Ferguson et al., *Cancer Res.* 1988, 48, 5956–5964; D. Beidler et al., *Cancer Res.* 1996, 56, 345–353).

All conjugates except 13 showed significant cytotoxicity (data in Table 2). Although they were not as active as paclitaxel and cephalomanine, 12 and 14–16 displayed comparable or better activity than epipodophyllotoxin derivatives in most tumor cell lines. Interestingly, 15, which is a conjugate of paclitaxel and 8, exhibited different cytotoxic activity from both precursors, suggesting that a novel mechanism of cell killing was achieved through conjugation. Compound 13, which has an epipodothyllotoxin conjugated at both the taxoid 2'- and 7-hydroxy groups, was less active. Thus, the taxoid 7-hydroxy group may be crucial for cytotoxic activity; a similar result was found previously by Mathew et al (A. Mathew et al., *J. Med. Chem.* 1992, 35, 145–151). Compared with the unconjugated components, 12, 15 and 16 showed enhanced activity against paclitaxel resistant cells (Table 3). Compounds 12, 13 and 15 were selected for further cytotoxicity evaluation in approximately 60 human tumor cell lines by NCI. The average log $GI_{50}$ values over all cell lines for each tumor type are presented in Table 4. Compound 12 showed the strongest inhibitory effects against a variety of tumor cell lines, especially leukemia, colon, and prostate cell lines.

In the topoisomerase assays, all three conjugates inhibited topo II in vitro but only 12 and 15 were intracellular poisons (Table 5). Compound 13, which contains two epipodothyllotoxin moieties, did not stimulate protein-DNA breaks in cells. However, in the topo II inhibitory assay, 13 was twofold more active than 12 and 15, and comparable to GL-331, suggesting that a free hydroxy group might play a role in drug transport into tumor cells.

TABLE 1

<sup>1</sup>H NMR Assignments of Taxoids and Their Conjugates

| Proton No. | 9 | 10 | 11 | 12 | 13 | 14 | 15 | 16 |
|---|---|---|---|---|---|---|---|---|
| Signals belonging to taxoid portion | | | | | | | | |
| 2 | 5.68 (d, 7) | 5.80 (d, 7) | 5.68 (d, 7) | 5.68 (d, 7) | 5.69 (d, 7) | 5.68 (d, 7) | 5.68 (d, 7) | 5.68 (d, 7) |
| 3 | 4.20 (d, 8) | 4.06 (d, 8) | 3.81 (d, 7) | 3.81 (d, 7) | 4.04 (dd, 7, 2) | 3.81 (d, 7) | 3.82 (d, 7) | 3.81 (d, 7) |
| 5 | 4.98 (d, 9) | 5.02 (d, 9) | 4.97 (d, 9) | 4.97 (d, 10) | 5.04 (br.d, 9) | 4.96 (d, 9) | 4.97 (dd, 8, 2) | 4.96 (d, 9) |
| 6□, □ | 1.90 (tt, 13, 3) | 1.92 (m) | 1.87 (m) | 1.88 (br.t, 13) | 1.92 (m) | 1.88 (m) | 1.88 (ddd, 16, 11, 2) | 1.88 (br.t, 13) |
| 7 | 4.45 (m) | 5.81 (dd, 10, 4) | 4.46 (m) | 4.44 (dd, 10, 7) | 5.82 (m) | 4.44 (m) | 4.45 (dd, 11, 7) | 4.45 (m) |
| 10 | 6.30 (s) | 6.38 (s) | 6.30 (s) | 6.30 (s) | 6.38 (s) | 6.30 (s) | 6.30 (s) | 6.30 (s) |
| 13 | 6.27 (t, 9) | 6.25 (t, 9) | 6.26 (br.t, 9) | 6.26 (t, 9) | 6.24 (t, 9) | 6.26 (br.t, 9) | 6.27 (t, 9) | 6.26 (br.t, 9) |
| 14□, □ | 2.14 (dd, 15, 9) | 2.17 (dd, 15, 9) | 2.55 (m) | 2.14 (dd, 15, 0) | 2.18 (m) | 2.55 (m) | 2.14 (dd, 15, 9) | 2.55 (m) |
|  | 2.34 (dd, 15, 9) | 2.38 (dd, 15, 9) |  | 2.33 (dd, 15, 9) | 2.36 (m) |  | 2.33 (dd, 15, 9) |  |
| 16-CH$_3$ | 1.23 (s) | 1.21 (s) | 1.26 (s) | 1.23 (s) | 1.26 (s) | 1.25 (s) | 1.24 (s) | 1.26 (s) |
| 17-CH$_3$ | 1.14 (s) | 1.18 (s) | 1.15 (s) | 1.14 (s) | 1.19 (s) | 1.14 (s) | 1.14 (s) | 1.15 (s) |
| 18-CH$_3$ | 1.97 (s) | 1.97 (s) | 1.82 (s) | 1.96 (s) | 1.97 (s) | 1.82 (s) | 1.96 (s) | 1.83 (s) |
| 19-CH$_3$ | 1.68 (s) | 1.95 (s) | 1.68 (s) | 1.68 (s) | 1.96 (s) | 1.68 (s) | 1.68 (s) | 1.68 (s) |
| 20□ | 4.32 (d, 84) | 4.37 (d, 8) | 4.30 (d, 8) | 4.31 (d, 9) | 4.37 (d, 8) | 4.30 (d, 8) | 4.31 (d, 9) | 4.29 (d, 8) |
| 20□ | 4.20 (d, 8) | 4.25 (d, 8) | 4.20 (d, 8) | 4.19 (d, 9) | 4.27 (d, 8) | 4.19 (d, 8) | 4.20 (d, 9) | 4.19 (d, 8) |
| 2' | 5.72 (d, 4) | 5.75 (d, 4) | 5.64 (d, 3) | 5.70 (d, 4) | 5.70 (d, 4) | 5.62 (br. s) | 5.71 (d, 4) | 5.65 (br. s) |
| 3' | 6.08 (dd, 10, 4) | 6.09 (dd, 9, 4) | 5.94 (dd, 9, 3) | 6.04 (dd, 9, 4) | 6.08 (dd, 9, 4) | 5.92 (br. s) | 6.05 (dd, 9, 4) | 5.92 (br. dd, 9, 3) |
| 3'-NH | 6.97 (d, 9.6) | 7.07 (d, 8) | 6.55 (d, 9) | 7.02 (d, 9) | * | 6.56 (d, 9) | 7.06 (d, 9) | 6.61 (d, 8) |
| 2-OBz(o) | 8.13 (d, 7) | 8.13 (d, 8) | 8.12 (d, 8) | 8.13 (d, 7) | 8.14 (d, 7) | 8.12 (d, 8) | 8.11 (d, 7.5) | 8.11 (d, 8) |
| 2-OBz(m) | 7.52 (t, 7) | 7.53 (d, 8) | 7.51 (t, 8) | 7.52 (d, 7) | 7.52 (d, 7) | 7.52 (d, 8) | 7.52 (d, 7.5) | 7.51 (t, 8) |
| 2-OBz(p) | 7.62 (m) | 7.64 (t, 8) | 7.62 (t, 8) | 7.62 (t, 8) | 7.64 (t, 7) | 7.62 (t, 8) | 7.61 (t, 7.5) | 7.61 (t, 8) |
| 7-OBz(o) | — | 7.93 (d, 8) | — | — | 7.97 (d, 8) | — | — | — |
| 7-OBz(m) | — | 8.07 (d, 8) | — | — | 7.81 (d, 8) | — | — | — |
| 2'-OBz(o) | 8.14 (d, 8) | 8.15 (d, 8) | 8.12 (d, 8) | 8.04 (dd, 7, 2) | 8.08 (d, 8) | 7.85 (d, 8) | 8.15 (d, 8) | 8.11 (br. d, 8) |
| 2'OBz(m) | 7.98 (d, 8) | 7.97 (d, 8) | 7.97 (d, 8) | 7.85 (dd, 7, 2) | 7.86 (d, 8) | 8.01 (d, 8) | 7.76 (d, 8) | 7.52 (br. d, 8) |
| 3'-Ph(o) | 7.45 (d, 8) | 7.48 (d, 8) | 7.40 (m) | 7.44 (d, 8) | 7.43 (d, 7) | 7.40 (m) | 7.43 (d, 8) | 7.40 (m) |
| 3'-Ph(m) | 7.41 (t, 8) | 7.42 (m) | 7.40 (br.s) | 7.41 (t, 8) | 7.47 (t, 7) | 7.40 (m) | 7.41 (t, 8) | 7.40 (m) |
| 3'-Ph(p) | 7.44 (t, 8) | 7.35 (dd, 7, 2) | 7.33 (t, 7) | 7.43 (d, 8) | 7.33 (br.t, 7) | 7.32 (m) | 7.42 (d, 8) | 7.32 (m) |
| NBz(o) | 7.76 (d, 8) | 7.77 (br.d, 8) | — | 7.75 (d, 8) | 7.75 (d, 7) | — | 7.76 (d, 8) | — |
| NBz(m) | 7.52 (br, t, 7) | 7.45 (m) | — | 7.51 (t, 7) | 7.47 (t, 7) | — | 7.51 (t, 7) | — |
| NBz(p) | 7.52 (br, t, 7) | 7.46 (m) | — | 7.52 (t, 7) | 7.53 (t, 7) | — | 7.52 (t, 7) | — |
| 1-OH | 1.89 (br. t, 11, 2) | 1.92 (br.s) | — | 1.97 (s) | 1.97 (s) | — | 1.96 (s) | — |
| 7-OH | 2.54 (br.s) | — | — | 2.49 (br.s) | — | — | 2.50 (br. s) | — |
| 2'OH | — | — | — | — | — | — | — | — |
| 4-OAc | 2.46 (s) | 2.49 (s) | 2.43 (s) | 2.44 (s) | 2.49 (s) | 2.41 (s) | 2.43 (s) | 2.41 (s) |
| 10-OAc | 2.23 (s) | 2.06 (s) | 2.23 (s) | 2.23 (s) | 2.07 (s) | 2.23 (s) | 2.22 (s) | 2.23 (s) |
| 2"-CH$_3$ | — | — | 1.97 (s) | — | — | 1.96 (br. s) | — | 1.96 (s) |
| 3" | — | — | 6.43 (br.q, 7) | — | — | 6.43 (br.q, 7) | — | 6.45 (br.q, 7) |
| 4"-CH$_3$ | — | — | 1.72 (d, 7) | — | — | 1.72 (d, 7) | — | 1.73 (d, 7) |
| CHO | 10.13 (s) | 10.10 (s), 10.12 (s) | 10.11 (s) | — | — | — | — | — |
| Signals belonging to epipodophyliotoxin portion | | | | | | | | |
| 1"' | | | | 4.61 (br. d, 4) | 4.71 (2H, d, 5) | 4.67 (br,s) | 4.62 (d, 5) | 4.61 (br.d, 4) |
| 2"' | | | | 3.13 (m) | 3.12 (2H, m) | 3.13 (m) | 3.14 (dd, 15, 5) | 3.14 (dd, 14, 4) |
| 3"' | | | | 3.11 (m) | 3.05 (2H, m) | 3.12 (m) | 3.02 (tdd, 15, 7, 4) | 3.04 (m) |
| 4"' | | | | 4.71 (d, 5) | 4.68 (2H, t, 4) | 4.71 (d, 5) | 4.73 (dd, 5, 5) | 4.73 (br.s) |
| 5"' | | | | 6.58 (s) | 6.39 (2H, s) | 6.59 (s) | 6.80 (s) | 6.80 (s) |
| 8"' | | | | 6.39 (s) | 6.60 (2H, s) | 6.39 (s) | 6.55 (s) | 6.54 (s) |
| 11"' | | | | 4.00, 4.27 (t, 9) | 4.26 (2H, m) | 4.20, 4.27 (t, 9) | 4.22 (td, 11, 5) | 4.01, 4.40 (t, 9) |
| | | | | | 4.00 (2H, m) | | 4.00 (td, 11, 5) | |
| OCH$_2$O | | | | 5.92, 5.98 (br. s) | 5.92, 5.98 (both 2H, each br.s) | 5.98 (br.s) | 5.92, 5.99 (d, 1) | 5.96, 5.98 (br.s) |

TABLE 1-continued

1H NMR Assignments of Taxoids and Their Conjugates

| Proton No. | 9 | 10 | 11 | 12 | 13 | 14 | 15 | 16 |
|---|---|---|---|---|---|---|---|---|
| 2'''', 6'''' | | | | 6.39 (s) | 6.38 (4H, s) | 6.39 (s) | 6.34 (s) | 6.34 (s) |
| $OCH_3X2$ | | | | 3.81 (s) | 3.81 (6H, s) | 3.81 (s) | 3.80 (s) | 3.80 (s) |
| CH=N | | | | 8.51 (s) | 8.51 (s), 8.53 (s) | 8.51 (s) | 8.57 (s) | 8.57 (s) |
| $NHC_6H_4$—N= | | | | — | — | — | 7.97, 8.07 (d, 9) | 7.97, 8.04 (d, 8) |

*Proton could not be assigned due to complexity of the spectrum.

TABLE 2

Cytotoxicity of 12–16 in Selected Human Tumor Cell Lines (ED50) (uM)

| Compound | KB | A549 | HCT-8 | CAKI-1 | MCF-7 | SK-MEL-2 | 1A9 (OVCAR) |
|---|---|---|---|---|---|---|---|
| 12 | 0.003 | 0.21 | 0.54 | >0.25 | 0.33 | >0.40 | 0.03 |
| 13 | 16.5 | $NA^1$ | NA | >4 | >4 | NA | ND |
| 14 | 0.03 | 0.70 | 2.78 | >5 | 1.23 | 8.90 | 0.14 |
| 15 | 0.23 | 2.80 | >0.1 | >4 | 1.86 | >40 | 0.30 |
| 16 | 1.40 | 3.55 | >40 | >10 | >5 | >40 | 1.12 |
| GL-331 | 1.86 | 0.48 | 3.38 | 1.80 | 9.29 | 5.95 | 0.20 |
| Etoposide | 0.20 | 1.95 | >5 | 2.2 | >5 | ND | 0.60 |
| Cephalomannine | 0.002 | 0.009 | 0.047 | >0.3 | 0.167 | 0.134 | 0.003 |
| Paclitaxel | 0.016 | 0.006 | 0.013 | $ND^2$ | ND | ND | 0.002 |

[1]NA = not active
[2]ND = not determined

TABLE 3

Cytotoxicity of 12–16 in Drug Resistant Cell Lines (Resistance Fold)

| Compound | KB-7d | KB-VCR | KB-CPT | PAX-10 | PAX-22 |
|---|---|---|---|---|---|
| 12 | 1 | 17 | 1 | 7 | 17 |
| 13 | 0.6 | —[1] | — | — | — |
| 14 | — | — | — | >36 | — |
| 15 | 1 | 8 | 1 | >17 | 8 |
| 16 | — | — | — | 7.5 | — |
| GL-331 | 2 | 3 | 1 | 13 | 8 |
| Etoposide | 119 | 153 | 1 | >16 | >16 |
| Cephalomannine | — | — | — | 40 | — |
| Paclitaxel | 1 | 15 | 1 | 24 | 24 |

[1]ND = not determined

TABLE 5

Topoisomerase II Inhibitory Activities of 12–16

| Compound | Inhibition of Topo II $IC_{100}$ (uM) | Cellular protein-DNA complex formation (%) |
|---|---|---|
| 12 | 100 | 8 +/− 2 |
| 13 | 50 | $NA^1$ |
| 14 | $NA^2$ | $NA^2$ |
| 15 | 100 | 25 +/− 11 |
| 16 | $NA^2$ | $NA^2$ |
| GL-331 | 50 | 134 +/− 7 |
| Etoposide | 100 | 100 |
| Cephalomannine | $NA^2$ | $NA^2$ |
| Paclitaxel | $NA^1$ | $NA^1$ |

[1]Not active at 50 uM
[2]not active at 100 uM.

TABLE 4

Cytotoxicity of 12–16 in NCI Human Tumor Cell Lines (log $GI_{50}$)[1]

| compd | leukemia | $NSCL^2$ | Colon | $CNS^3$ | melanoma | ovarian | renal | prostate | breast |
|---|---|---|---|---|---|---|---|---|---|
| 12 | −7.60 | −6.58 | −7.20 | −6.93 | −6.29 | −6.55 | −6.13 | −7.22 | −6.56 |
| 13 | −4.95 | −5.78 | −4.90 | −5.20 | −5.16 | −5.03 | −5.08 | −5.06 | −4.93 |
| 15 | −6.02 | −5.50 | −5.12 | −5.54 | −5.01 | −4.95 | −5/88 | −5.06 | −4/96 |

[1]The data were provided by the NCI.
$GI^{50}$ is the concentration that caused 50% inhibition of tumor cell growth.
[2]Non-small cell lung cancer.
[3]Central nervous system cancer.

The foregoing is illustrative of the present invention, and is not to be construed as limiting thereof. The Invention is defined by the following claims, with equivalents of the claims to be included therein.

We claim:

1. A compound according to formula I:

(I)

wherein:

$T_1$ is a taxoid group of Formula II:

(II)

wherein $R_1$ is $C_6H_5$, and $R_2$ is O;

L is a linking group; and $T_2$ is a substituent selected from the group consisting of epipodophyllotoxin, amsacrine, ellipticine, anthracycline antibiotic, mitoxantrone, mitomycin, quinolone, and colchicine groups;

or a pharmaceutically acceptable salt thereof.

2. A compound according to claim 1, wherein $T_2$ is an epipodophyllotoxin group of formula III-A:

(III-A)

wherein:

$R_{10}$, $R_{11}$, $R_{12}$, $R_{13}$, $R_{15}$, and $R_{16}$ are each independently selected from the group consisting of H, alkyl, hydroxy, alkoxy, alkylhydroxy, and halo;

$R_{14}$ is selected from the group consisting of H, alkyl, hydroxyl, alkoxy, alkylhydroxy, halo, and phosphate salt; and $R_{17}$ is NH or is absent.

3. A compound according to claim 1, wherein $T_2$ is an amsacrine group of formula III-B:

(III-B)

wherein $R_{20}$ and $R_{21}$, are each independently selected from the group consisting of H, alkyl, hydroxy, alkoxy and alkylhydroxyl;

$R_{22}$ and $R_{23}$ are each independently selected from the group consisting of H, alkyl, hydroxy, alkoxy, alkylhydroxy, and halo; and $R_{24}$ is NH or is absent.

4. A compound according to claim 1, wherein $T_2$ is an ellipticine group of formula III-C (III-C)

wherein:

$R_{30}$ is H or alkyl, or is absent;

$R_{31}$ is H, alkyl, hydroxy, alkoxy, alkyhyroxy, halo, or —C(O)—N($R_{36}$)—($CH_2$)$_n$—N($R_{37}$)($R_{38}$) wherein $R_{36}$, $R_{37}$, and $R_{38}$ are each independently selected from the group consisting of H and alkyl and n is an integer from 1 to 6;

$R_{32}$ and $R_{33}$ are each independently selected from the group consisting of H, alkyl, hydroxy, alkoxy, alkylhydroxy, and halo;

$R_{34}$ is H or alkyl; and $R_{35}$ is O or is absent.

5. A compound according to claim 1, wherein $T_2$ is an anthracycline antibiotic group of formula III-D:

(III-D)

wherein:
$R_{40}$ is H, alkyl, hydroxy, alkoxy, alkylhydroxy, or halo;
$R_{41}$ is hydroxyl O— or a covalent bond;
$R_{42}$ is alkyl, alkylhydroxyl, $CH_2O$— or $CH_2$—; and
$R_{43}$ and $R_{44}$ are each independently selected from the group consisting of H and hydroxy;
$R_{45}$ is hydroxy or $NH_2$; and
$R_{46}$ is H or halo;
subject to the provisos that if $R_{41}$ is not O— or a covalent bond, then R42 is $CH_2O$— or $CH_2$—; and if R42 is not $CH_2O$— or $CH_2$— then $R_{41}$ is O— or a covalent bond.

6. A compound according to claim 1, wherein $T_2$ is a mitoxantrone group of formula III-E (III-E)

wherein
$R_{50}$, $R_{51}$, $R_{52}$ and $R_{53}$ are each independently selected from the group consisting of OH or O—; subject to the proviso that one of $R_{50}$, $R_{51}$, $R_{52}$ and $R_{53}$ is O—.

7. A compound according to claim 1, wherein $T_2$ is a mitomycin group of formula III-F:

(III-F)

wherein:
X is $NH_2$, NH—, or an aliphatic amine;
$R_{71}$ is alkyl or halo;
$R_{72}$ is hydroxy or alkoxy;
$R_{73}$ is H or absent; and
Y is H or alkyl.

8. A compound according to claim 1, wherein $T_2$ is a colchicine group of formula III-G:

(III-G)

$R_{60}$ and $R_{61}$ are each independently H, alkyl, hydroxy, O—, or alkoxy;
$R_{62}$ is H, $NH_2$, NH—, OH, O—, =O, or $NHCOCH_3$, and X is S or O, subject to the proviso that one of $R_{60}$ or $R_{61}$ is O—, or $R_{62}$ is either NH— or O—.

9. A compound according to claim 1, wherein $T_2$ is a quinolone group of formula III-H:

(III-H)

wherein:
$R_{81}$ is selected from the group consisting of H, hydroxy, lower alkyl, lower alkoxy, hydroxy, halo, and amino;
$R_{82}$ is is selected from the group consisting of H, hydroxy, lower alkyl, lower alkoxy, hydroxy, halo, and amino;
$R_{83}$ is is selected from the group consisting of H, hydroxy, lower alkyl, lower alkoxy, hydroxy, halo, and amino;
$R_{84}$ is is selected from the group consisting of H, hydroxy, lower alkyl, lower alkoxy, hydroxy, halo, and amino;
$R_{85}$ is each independently selected from the group consisting of H, hydroxy, lower alkyl, lower alkoxy, hydroxy, halo, and amino; and
n is 0–4.

10. A compound according to claim 1, wherein L is a covalent linking group of the formula —$L_a$—$L_b$— where $L_b$ is present or absent and $L_a$ and $L_b$ are each independently selected from the group consisting of:

-continued wherein:
a is 0 to 3 and b is 0 to 3; and
$R_{70}$ is selected from the group consisting of alkylene, alkenyl, and arylenyl.

11. A pharmaceutical formulation comprising a compound according to claim 1 in a pharmaceutically acceptable carrier.

12. A pharmaceutical formulation according to claim 11, wherein said carrier is an aqueous carrier.

13. A method of treating a tumor, comprising administering to a subject in need thereof a treatment effective amount of a compound according to claim 1.

14. A method according to claim 13, wherein said tumor is a solid tumor.

15. The method according to claim 13, wherein said tumor is caused by a cancer selected from the group consisting of lung cancer, colon cancer, central nervous system cancers, melanoma, ovarian cancer, prostate cancer and breast cancer.

16. The method according to claim 13, wherein said tumor is caused by breast cancer.

17. The method according to claim 13, wherein said tumor is caused by prostate cancer.

18. A method of treating cancer in a subject in need thereof, said method comprising administering to said subject an effective cancer treating amount of a compound according to claim 1.

19. A method according to claim 18, wherein said cancer is selected from the group consisting of small cell lung cancer, testicular cancer, lymphoma, leukemia, esophageal cancer, stomach cancer, colon cancer, breast cancer, central nervous system cancer, liver cancer and prostate cancer.

* * * * *

UNITED STATES PATENT AND TRADEMARK OFFICE
CERTIFICATE OF CORRECTION

PATENT NO.   : 6,624,317 B1
DATED        : September 23, 2003
INVENTOR(S)  : Lee et al.

It is certified that error appears in the above-identified patent and that said Letters Patent is hereby corrected as shown below:

<u>Title page,</u>
Item [75], Inventors, please correct the inventors as follows:
-- Qian Shi, Chapel Hill, NC (CN)
   Hui-Kang Wang, Chapel Hill, NC (CN) --

<u>Column 22, lines 49-66, through Column 23, lines 1-32,</u>
Please correct claim 10 to read:
10 (original). A compund according to claim 1, wherein L is a covalent linking group of the formula $-L_a-L_b-$ where $L_b$ is present or absent and $L_a$ and $L_b$ are each independently selected from the group consisting of:

wherein:
    A is 0 to 3 and b is 0 to 3; and
    $R_{70}$ is selected from the group consisting of alkylene, alkenyl, and arylenyl.

Signed and Sealed this

Twenty-fourth Day of August, 2004

JON W. DUDAS
*Director of the United States Patent and Trademark Office*